US005776985A

United States Patent [19]
Weglicki et al.

[11] Patent Number: 5,776,985
[45] Date of Patent: Jul. 7, 1998

[54] FLUORINATED PROPRANOLOL AND RELATED METHODS

[75] Inventors: William B. Weglicki, Potomac; L T. Mak, Germantown, both of Md.; Hassan Y. Aboul-Enein, Riyadh, Saudi Arabia

[73] Assignee: The George Washington University, Washington, D.C.

[21] Appl. No.: 748,894

[22] Filed: Nov. 14, 1996

Related U.S. Application Data

[60] Provisional application No. 60/006,835, Nov. 16, 1995.
[51] Int. Cl.$^6$ .................... A61K 31/135; C07C 217/64
[52] U.S. Cl. ............................... 514/652; 564/349
[58] Field of Search ..................... 564/349; 514/652

[56] References Cited

U.S. PATENT DOCUMENTS 3,337,628   8/1967   Crowther et al. .................. 564/349

OTHER PUBLICATIONS

Farooqi et al., Chemical Abstracts, vol. 124, abstract 175051y, 1996.

*Primary Examiner*—Richard L. Raymond

[57] ABSTRACT

Fluorinated beta blockers, such as propranolol, are presented with amplified antioxidant effects and various levels of beta blocking effects. Mixtures are also presented of fluorinated antioxidant drugs, such as propranolol, with fluorinated antioxidant non-beta blocking analogs of the same drugs. Methods of treatment of disease by the use of the fluorinated drugs and the mixtures are presented.

21 Claims, 12 Drawing Sheets

| COMPOUND | R1 | R2 |
|---|---|---|
| PROPRANOLOL, Ia | TO C16 ON THE MAIN STRUCTURE — C33 with 35H, 36H, 37H | TO C16 ON THE MAIN STRUCTURE — C34 with 38H, 39H, 40H |
| TRIFLUOROETHYL-PROPRANOLOL, Ib | TO C16 ON THE MAIN STRUCTURE — C33 with F35, F36, F37 | H(34) |
| PENTAFLUOROPROPYL-PROPRANOLOL, Ic | TO C16 ON THE MAIN STRUCTURE — C33 (F36, F37) — C with F38, F39, F40 | H(34) |
| HEPTAFLUOROBUTYL-PROPRANOLOL, Id | TO C16 ON THE MAIN STRUCTURE — C33 (F36, F37) — C38 (F40, F41) — C39 with F41, F42, F43 | H(34) |

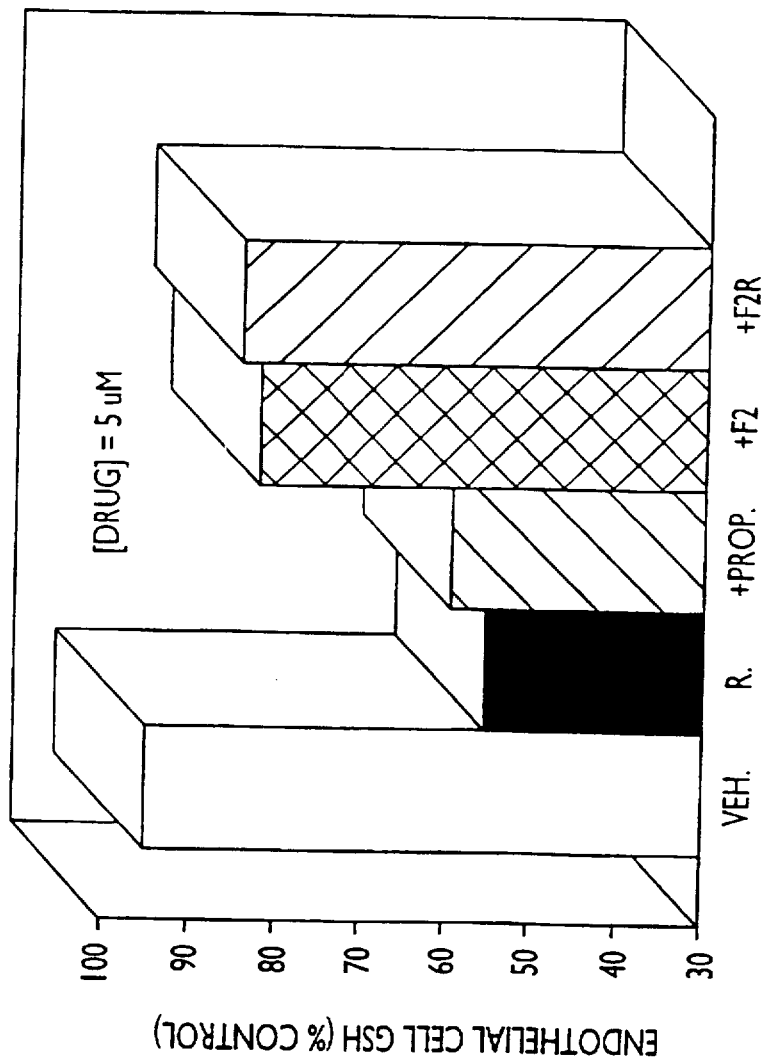

L - PROPRANOLOL

D - PROPRANOLOL

FLUORINATED PROPRANOLOL AND RELATED METHODS

This patent claims priority of U.S. Provisional Application No. 60/006,835, filed Nov. 16, 1995, and No. 60/008, 790, filed Dec. 18, 1995.

BACKGROUND OF THE INVENTION

The field of this invention is pharmaceuticals which act as beta blockers and pharmaceuticals that act as antioxidants. Specifically, this invention relates to beta blockers with amplified and controlled antioxidant properties.

Beta blockers such as various forms of propranolol are known. It is known that a variety of heart and hypertension problems can be treated with beta blockers. However, an excessive treatment of beta blockers can cause undesirable side effects in patients.

Antioxidant agents are also known. It is also known that treatment by antioxidants may be used to treat similar and related heart and hypertension problems.

There has been some knowledge of incidental antioxidant characteristics of some forms of beta blockers. However, the prior art has not examined the possibility of amplified and controlled antioxidant characteristics of the same pharmaceuticals which are used for beta blocker effects. The prior art has not investigated possible synergistic effects of treating hypertension, heart failure and other heart disorders with a combination of antioxidants and beta blockers, and, in particular, no work has been done to develop single pharmaceuticals with both amplified antioxidant and controlled beta blocker effects.

II. SUMMARY OF THE INVENTION

It is an object of the present invention to amplify and control the antioxidant effect of beta blockers.

It is an object of the present invention to mix beta blocker forms of propranolol with nonbeta blocker forms of propranolol, all with antioxidant effects or amplified antioxidant effects, to obtain a variety of mixtures with antioxidant effects which have a controlled range of beta blocker potency. An object of this, in turn, is to allow synergistic application of amplified antioxidant effects and beta blocking effects to treat a variety of medical conditions, including, for example, heart ailments, heart failure, hypertension and inflammatory processes, while controlling the undesirable side effects of excessive beta blockers for the individual patients.

As part of the present invention, the inventors discovered significant membrane antioxidant activity for some fluorinated propranolol analogs. The antioxidant potency of these preparations increases with the degree of fluorination. Experimental results indicate that different isomers of propranolol (some of which may be pharmacologically active as beta blockers and some of which may be pharmacologically inactive as beta blockers) display equipotent antioxidant activity. That is, their antioxidant activity is independent of their pharmacological beta blocker activity.

Free radicals in the cell membranes cause lipid peroxidative damage and protein oxidative damage. Antioxidants neutralize the free radicals before they can cause this damage or may block the early "chain reaction" of peroxidation in the cell membranes. Fluorination of propranolol increases the lipophilicity of the propranolol analogs and thereby causes the higher partitioning of the antioxidant agents into the biomembranes of cells; therefore, these fluorinated propranolol beta blockers have greater antioxidant effect than the unfluorinated propranolols, because the fluorinated agents enter the membrane in greater quantity than the unfluorinated propranolols.

Since free radicals are known to promote a number of cardiovascular and neurological diseases, including ischemia/reperfusion, aging, neurodegeneration, atherogenesis, inflammation and others, use of these fluorinated beta blocking agents provide additional beneficial effects as antioxidants where the increased free radical production is an important component of the disease pathogenesis.

The present invention includes fluorinated propranolol analogs and methods of use as simultaneous beta blockers and amplified antioxidants for the treatment of heart failure, hypertension, and related diseases.

The present invention further includes mixtures of (1) fluorinated antioxidant non-beta blocking isomers of propranolol, with (2) fluorinated antioxidant beta blocking isomers of propranolol, in a range of ratios. This range of mixtures offers a range of choice of beta blocking intensity to correspond to a selected level of antioxidant activity, thereby avoiding excessive beta blocking for an individual case for a desired antioxidant impact. That is, for a given antioxidant impact, the simultaneous beta blocker impact can be controlled.

Potential disadvantages of use of fluorinated antioxidant beta blocking propranolols may include excessive beta blockade at higher dosage. The mixtures of the present invention offer choices that avoid the problems associated with excessive beta blocking, while achieving the targeted antioxidant benefit. This fluorination method may be applied to other beta blocking agents such as aterolol, metoprolol, and similar drugs, to enhance their lipophilicity and positioning into biological membranes.

III. BRIEF DESCRIPTION OF THE DRAWINGS

FIG. 1 shows the chemical structure of: propranolol (1a), trifluoroethyl-propranolol (1b), pentafluoropropyl-propranolol (1c), heptafluorobutyl-propranolol (1d). The schematic illustrates the common structure together with the numbers of the atoms. The table below the schematic gives the side chains R1 and R2 in the four molecules.

FIG. 5 shows the distribution of electrostatic potential in a) propranolol, b) trifluoroethyl-propranolol, c) pentafluoropropyl-propranolol, and d) heptafluorobutyl-propranolol. This view is perpendicular to the 3° axis of each molecule. The changes in the dotted contours represent the negative values.

Figure 6:
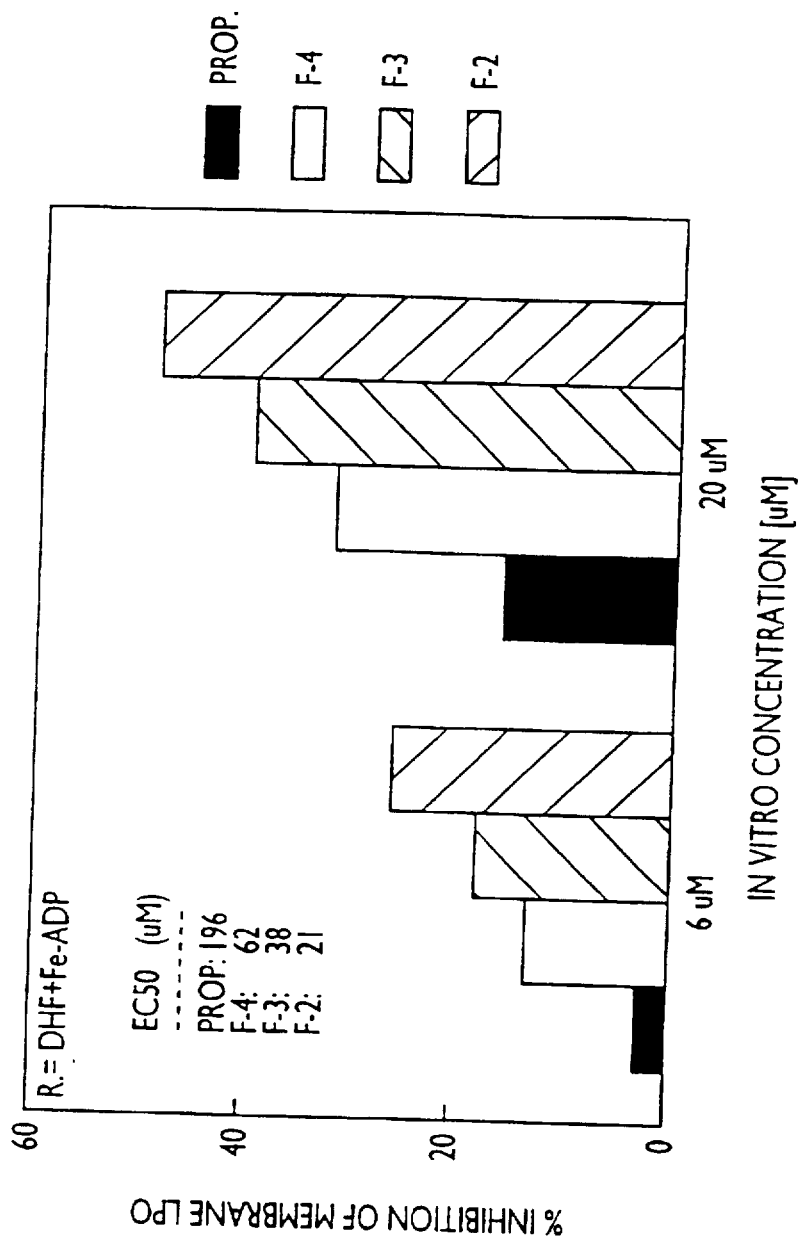

FIG. 6 shows the antioxidant activities of fluorinated propranolol analogs.

Figure 7:
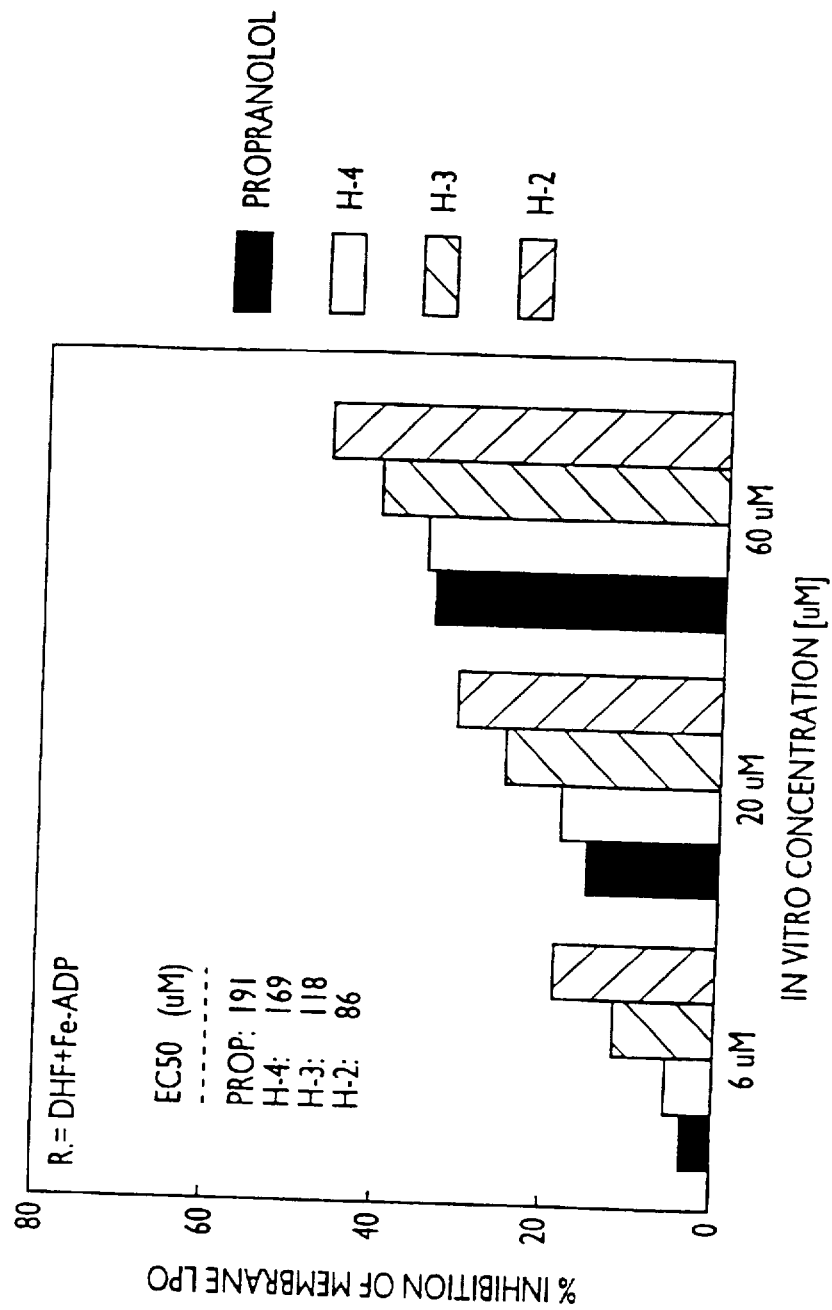

FIG. 7 shows the antioxidant activities of nonfluorinated propranolol analogs.

FIG. 8 shows the protective effects of F2 and F2-R on R.(DHF+Fe)-induced loss of endothelial cell glutathione (GSH).

Figure 9A:
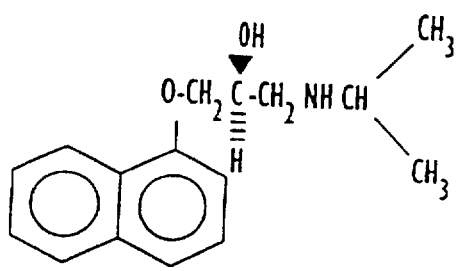
Figure 9B:
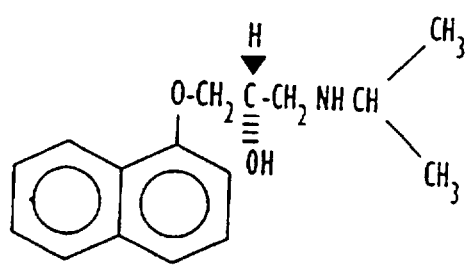

FIG. 9 shows the molecular structure of D-propranolol, and L-propranolol, which are both prior art.

Table 1 shows optimized energies of the molecules.

Table 2 shows coordinates of propranolol (1a).

Table 3 shows coordinates of trifluoroethyl-propranolol (1b).

Table 4 shows coordinates of pentafluoropropyl-propranolol (1c).

Table 5 shows coordinates of heptafluorobutyl-propranolol (1d).

Table 6 shows fluorinated propranolol analogs which are part of the present invention.

Table S1 shows important bond angles (°) for the fluorinated analogs.

Table S2 shows important torsion angles (°) for the fluorinated analogs.

Table S3 shows dipole moments of the molecules.

IV. DESCRIPTION OF PREFERRED EMBODIMENTS

FIG. 9 shows the molecular structure of D-propranolol (i.e., right or R-propranolol) and L-propranolol (i.e., left or S-propranolol), which are both prior art. L-propranolol is a beta blocker, that is, it is pharmacologically active. D- (or right-) propranolol is not a beta-blocker.

Table 6 shows the molecular structure of the fluorinated propranolol analogs, which are part of the present invention.

The inventors have found that D- and L-propranolol have about the same anti-oxidant potency.

The fluorination of propranolol (including both the D and L forms), or any other beta blockers, enhance their antioxidant potency and protect cardiovascular, neurological and other tissues from free radical-mediated injury. Clinical problems (such as heart failure, myocardial infarction, ischemia/reperfusion injury, stroke, and related diseases), where excess free radicals contribute to mechanisms of injury, benefit from treatment by fluorinated beta blockers, including treatment by a combination of fluorinated D-propranolol and fluorinated L-propranolol.

Chemical modifications include variable degrees of fluorination of these molecules to provide variable clinical efficacy.

The new combination of a fluorinated active beta blocker (e.g., L-propranolol, at 5–10% of a full dose), with a fluorinated inactive beta blocker (e.g., D-propranolol at 95–90% of a full dose) enhances antioxidant potency without excess beta blockade, and increases the safety margin of therapy. This is because excess beta blockade may depress cardiac function to unsafe levels, for example, for those with heart failure.

Both oral and other methods of administration (e.g., by intravenous infusion, topical, aerosol, or by organ preservation fluids) can be used. The therapeutic strategies include delivery of fluorinated antioxidant doses combined with effective beta blocking doses to maintain the patient on adequate beta blockade, while enhancing greatly the antioxidant therapy. In those clinical conditions where beta blockade may not be indicated, the non-beta blocking form (e.g., fluorinated D-propranolol) of the fluorinated drug may be administered alone or as an adjunct to other therapies, to treat diseases including thrombolysis, organ preservation,
heart failure, restenosis of angioplasty arteries, inflammatory processes (e.g. in skin, lungs, and eyes) and other conditions.

Molecular Structure

Studies of the theoretical geometrical structure of propranolol and three of its fluorinated derivatives: 1-(2,2,2-trifluoroethylamino)-3-(1-naphthyloxy)-2-propanol [trifluoroethyl-propranolol], 1-(2,2,3,3,3-pentafluoropropylamino)-3-(1-naphthyloxy)-2-propanol [pentafluoropropyl-propranolol], and 1-(2,2,3,3,4,4,4-heptafluorobutylamino)-3-(1-naphthyloxy)-2-propanol [heptafluorobutyl-propranolol]. The semi-empirical method, AM1 was used to optimize the structures. In the minimum energy state the geometries of the naphthyl moiety and the non-fluorinated portions of the analogs are quite similar to that of the parent. Dipole moments, charge density distributions, and electrostatic potential distributions all point to the significance of the ether oxygen in all four compounds and the increasing contribution of the side chain terminal to the activity of the molecule with increasing number of fluorines.

Propranolol, chemically known as 1-isopropylamino-3-1-naphthyloxy)-2-propanol (see FIG. 1a) is the model parent drug for non-selective β-blockers, a "pure" antagonist o catecholamines at the receptor sites. It has been used i) tc chronically lower blood pressure in (mild to moderate hypertension, ii) to prevent reflex tachycardia in severe hypertension, iii) to reduce intraocular pressure in glaucomatous eyes, iv) to reduce the frequency of anginal episode and improve exercise tolerance in many patients with angina, v) in the acute phase of a myocardial infarction to limit infarct size (a controversial use), vi) in the treatment o both supraventricular and ventricular arrhythmias, vii) to increase stroke volume in obstructive cardiomyopath; patents, viii) to inhibit peripheral conversion of thyroxine t triiodothyronine (besides β-blockade), ix) to reduce th frequency and intensity of migraine headaches, x) to reduc somatic manifestations of anxiety and xi) to treat alcohc withdrawal. The principal toxicities of propranolol resul from the blockade of cardiac, vascular, or bronchia β-adrenoceptors. Most important predictable untoward reac tions are in patients with reduced myocardial reserve asthma, peripheral vascular insufficiency, and diabete: Some patients experience a beta blocker withdrawal syn drome when discontinued after a long use. The manifesta tions of this are anxiety, tachycardia, increased intensity c angina, heart attack, or increase in blood pressure. Thes side effects of propranolol are not desired.

Figures 1A, 1B:
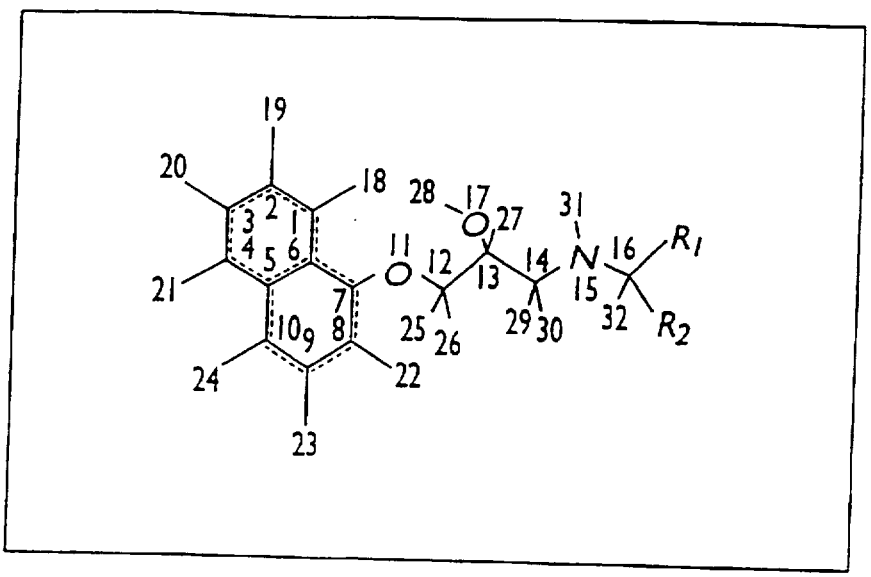

In search for compounds with better activity, some flu orinated derivatives of propranolol have been synthesized b the inventors, the structures of three of which are give herein, and are shown in FIGS. 1b to 1d, namely, 1-(2,2,2 trifluoroethylamino)-3-(1-naphthyloxy)-2-propanol (1i known as trifluoroethyl-propranolol), 1-(2,2,3,3,3 pentafluoropropylamino)-3-(1-naphthyloxy)-2-propan( (1c, known as pentafluoropropyl-propranolol), and 1-(2,2, 3,4,4,4-heptafluorobutylamino)-3-(1-naphthyloxy)-2 propanol (1d known as heptafluorobutylpropranolol Herein is described the computed atomic structure of pr pranolol and these three fluorinated analogs. This structur geometry is not known in the prior art and is part of th present invention.

The four structures above were created by the invento using HyperChem for Windows and optimized with a sem empirical technique, namely AM1. The Polak-Ribiere co jugate gradient method was used for optimization. Tl minimum energy states (with minimum binding energy) th were achieved were as shown in Table 1.

Geometrics

The geometrical coordinates of propranolol together with the charges on each atom are presented in Table 2. Similar information about the fluorinated derivatives is given in Tables 3 to 5. All the coordinates and distances in this paper are in angstroms (A). Except where significant, the particulars of the hydrogen atoms are not given here, and can be obtained from the authors.

The naphthyl moiety in all the compounds is flat. The bond angles of the naphthyl group are all approximately 120° each with minimal torsion within the rings. All the other bond angles range between 105° and 125°. In propranolol, the side chain zigzags around an axis in the plane of the naphthyl group (view a in FIG. 2). If the molecule is turned to view it from a side so that the naphthyl moiety becomes a straight line (view b in FIG. 2), the side chain is also more or less a straight line with its axis making an angle of approximately 173.5° with the plane of the naphthyl group. Keeping the rings flat and viewing the molecule such that the side chain goes into the plane of the paper perpendicularly (view c in FIG. 2), the bond with O17 atom (oxygen of the hydroxyl group) makes an angle of about −63° and the bond of the C34 atom an angle of about 121° with the plane of the rings.

Figure 2A:
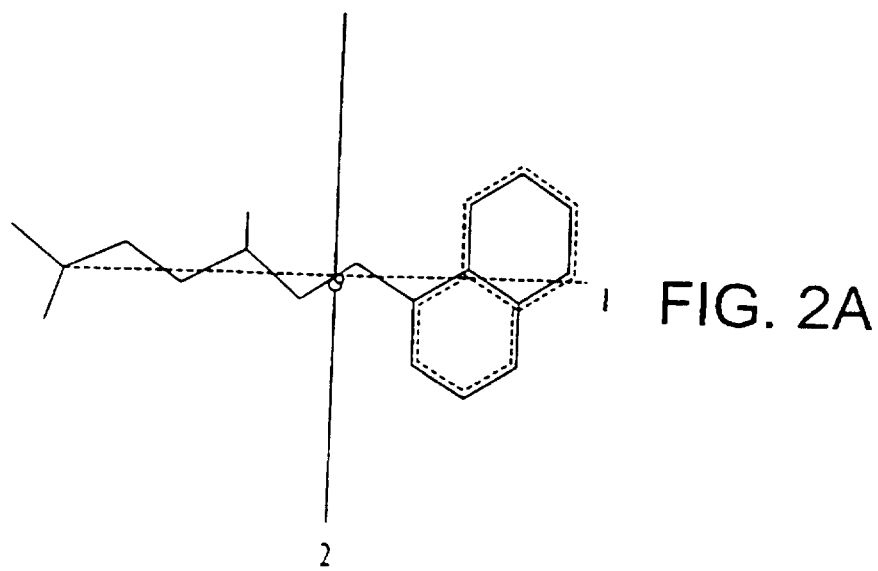
FIG. 2 shows propranolol viewed perpendicular to its a) longitudinal (primary or 1°) axis, b) secondary (2°) axis, and c) tertiary (3°) axis.
Figure 2B:
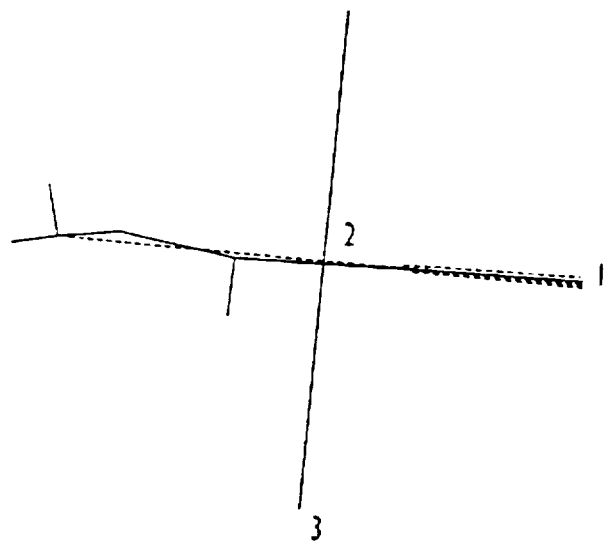
Figure 2C:
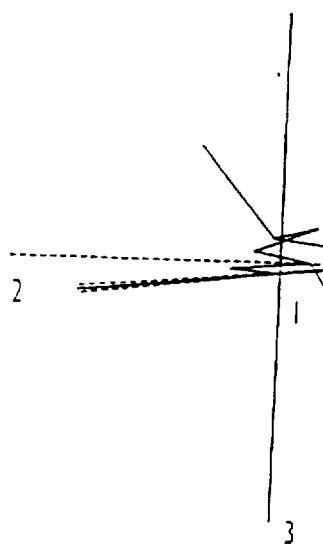
Figure 3A:
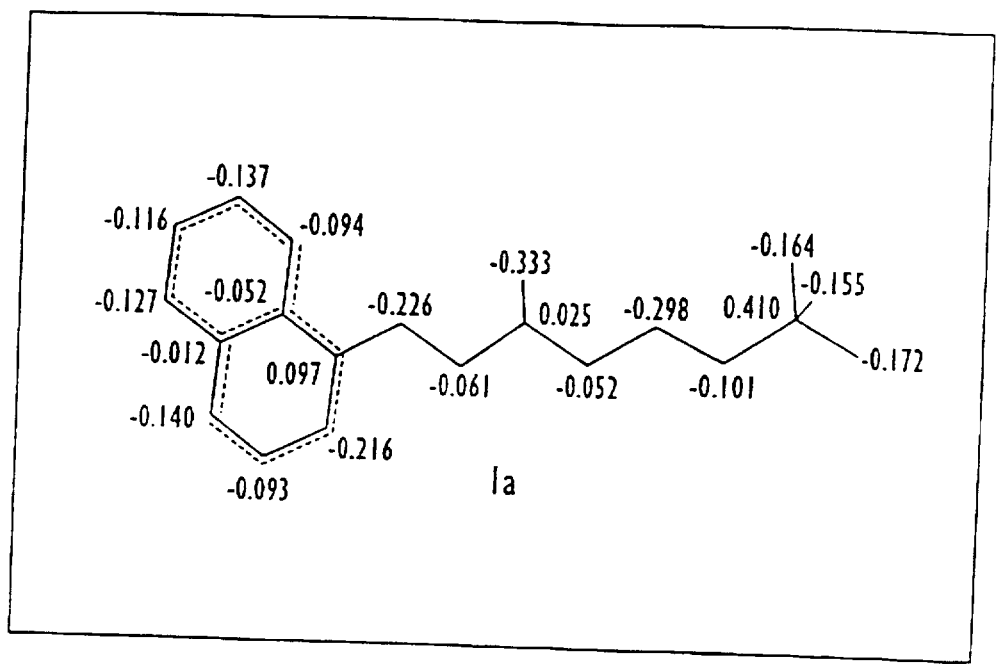
FIG. 3 shows the atomic charges and the structure of a) propranolol, b) trifluoroethyl-propranolol, c) pentafluoropropyl-propranolol, and d) heptafluorobutyl-propranolol.
Figure 3B:
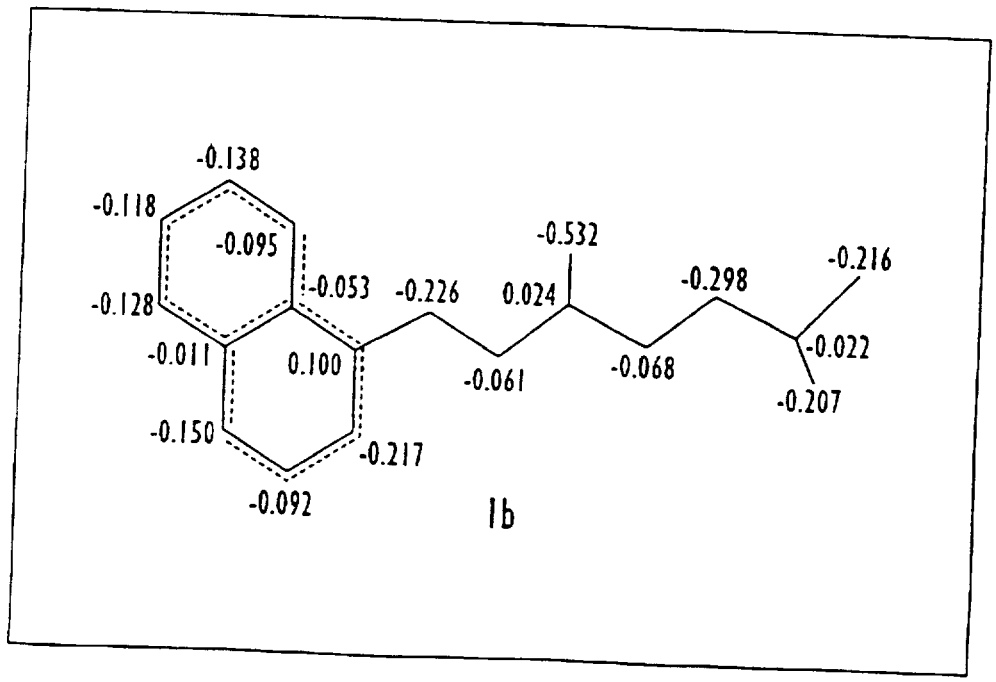
Figure 3C:
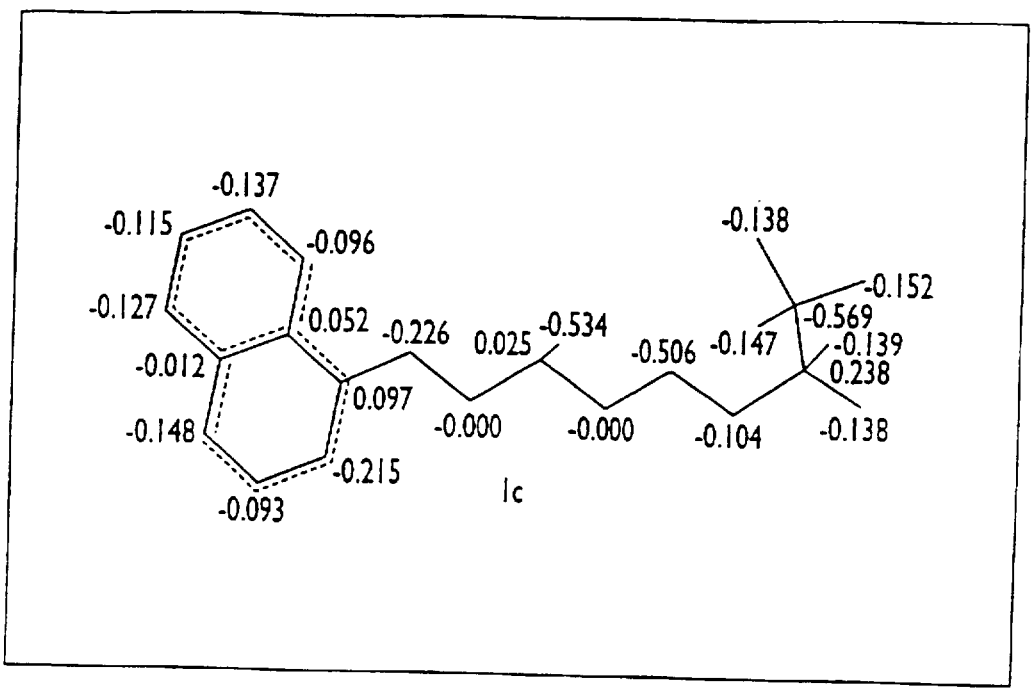
Figure 3D:
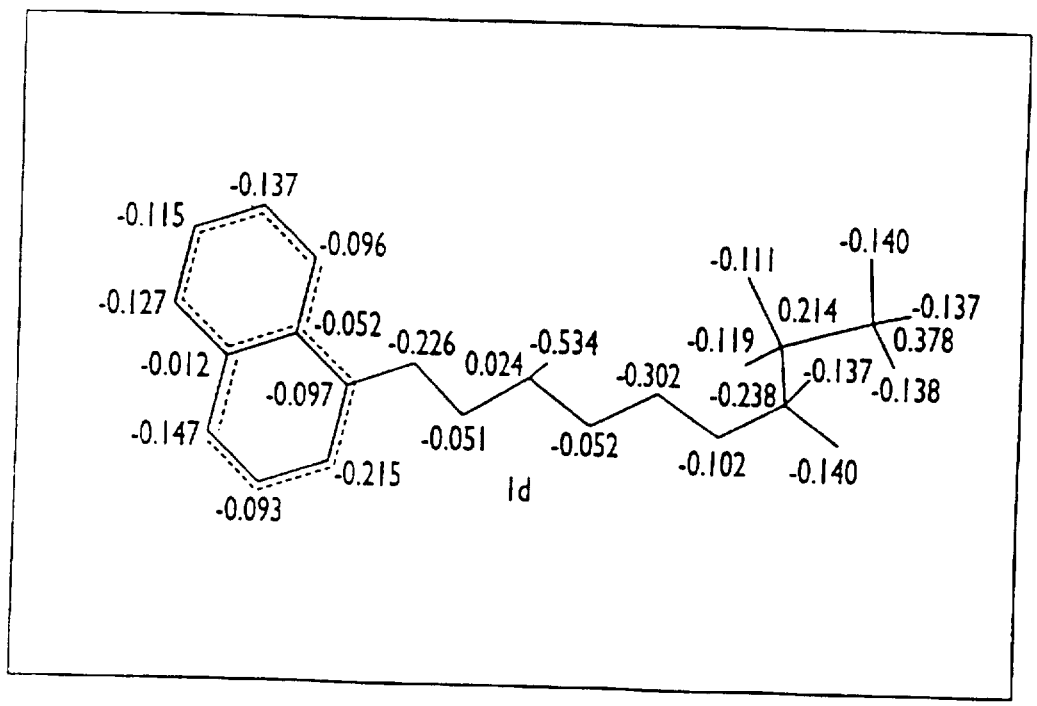
Figure 4B:
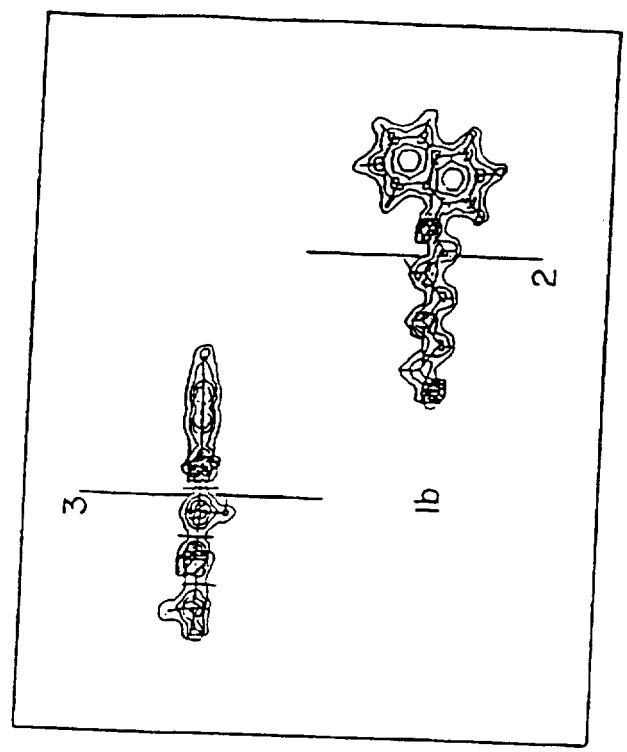
FIG. 4 shows the distribution of charge densities in a) propranolol, b) trifluoroethyl-propranolol, c) pentafluoropropyl-propranolol, and d) heptafluorobutyl-propranolol. For each molecule two views are presented, one perpendicular to the 2° axis and the other perpendicular to the 3° axis.
Figure 4A:
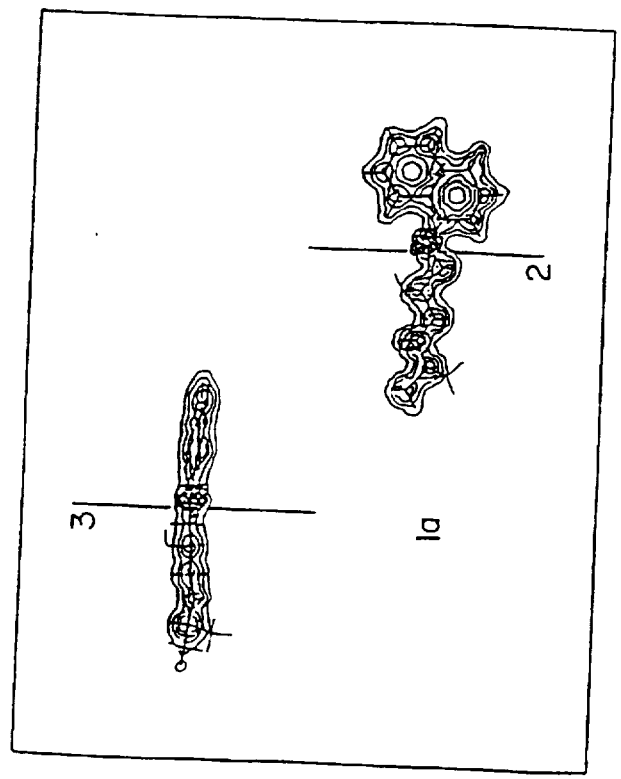
Figure 4D:
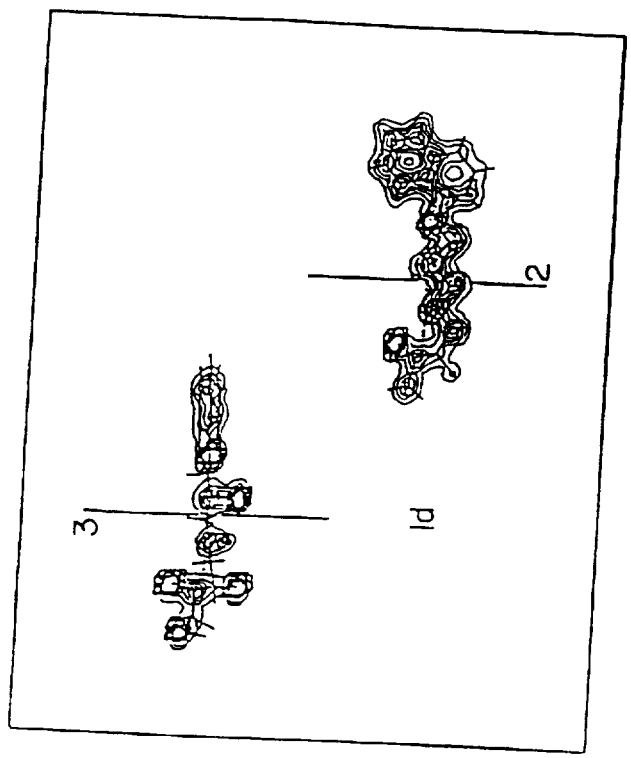
Figure 4C:
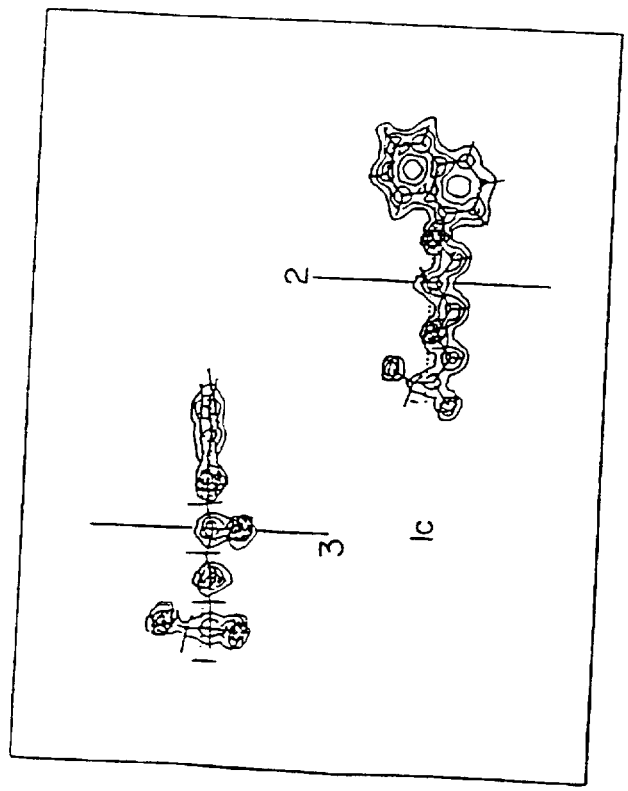
Figure 5B:
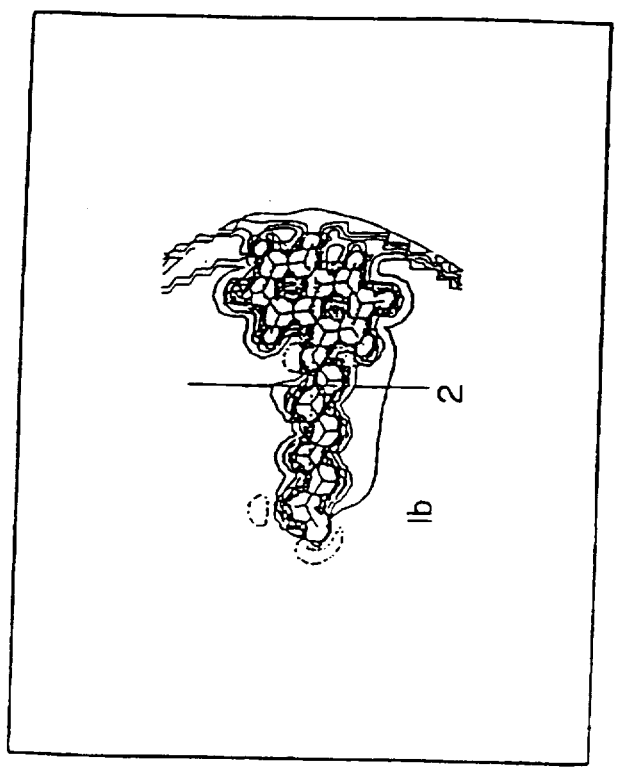
Figure 5A:
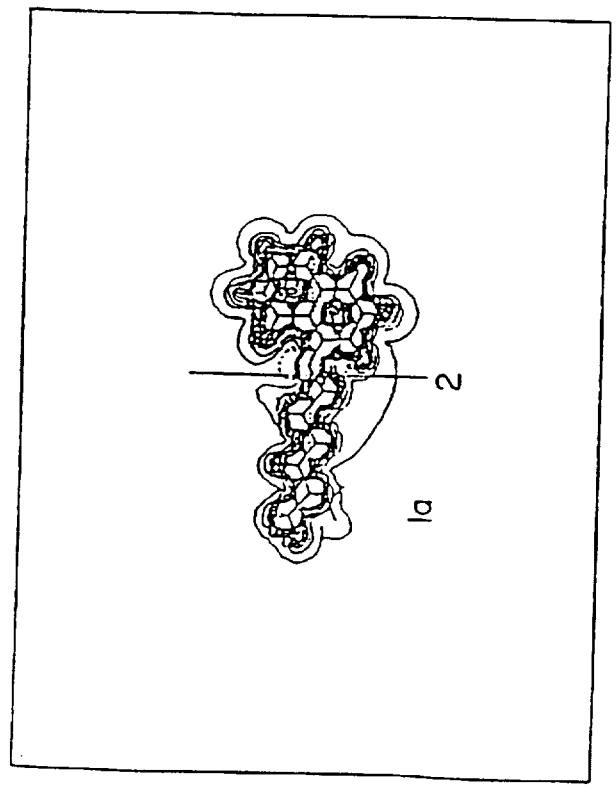
Figure 5D:
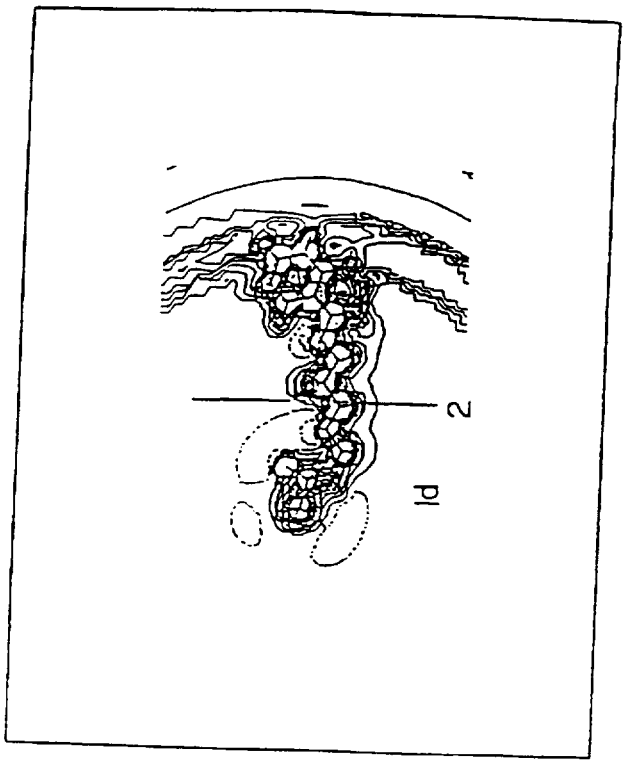
Figure 5C:
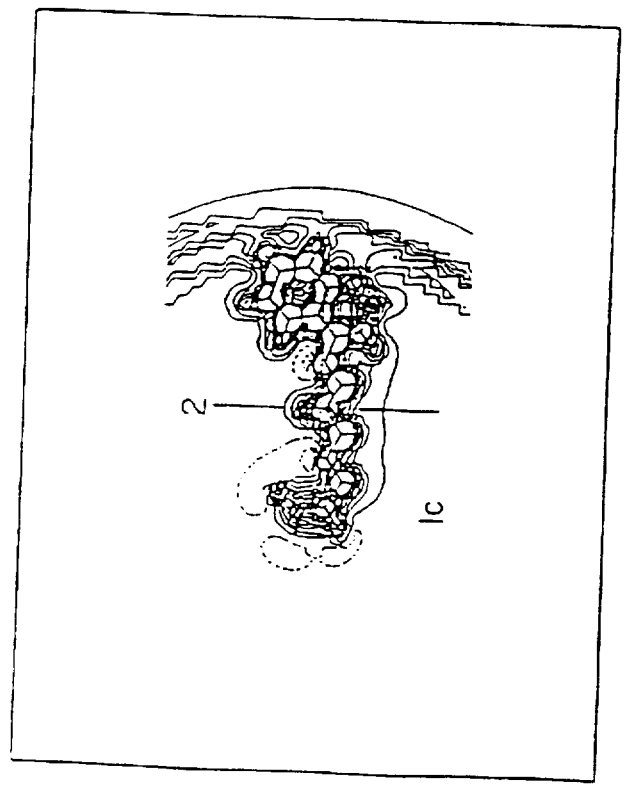

In 1b, the side chain zigzags in a similar way as in view a (FIG. 2) of the parent and its axis makes an angle of approximately 178.5° with the plane of the rings (in a view similar to view b of FIG. 2). While, when the side chain projects perpendicularly into the paper plane (like view c in FIG. 2) the bond with O17 atom makes about 66°, the C36 atom an angle of about 45.5° and the bond with C37 atom an angle of about −63.5° with the plane of the rings.

In 1c, zigzagging of the non-fluorinated portion of the side chain is similar to the parent (like view a in FIG. 2) and its axis makes an angle of approximately 177.5° with the plane of the rings (like in view b of FIG. 2). The —CF$_3$ group projects almost perpendicularly to the rest of the side chain (i.e., the non-fluorinated portion) in the direction opposite to that of the O17 atom. When viewed from the side with the side chain going perpendicularly into the paper plane (like in view c of FIG. 2) the bond with the O17 atom makes an angle of almost −118°, the bond of the C35 atom of almost −132°, and the bond of C37 atom of almost 115° with the plane of the rings.

In 1d, the zigzagging of the non-fluorinated portion is similar to the parent (like in view a of FIG. 2) and the axis of the non-fluorinated portion of the side chain makes an angle of about 178.5° with the plane of the rings (like in view b of FIG. 2), the first portion of the fluorinated region of the side chain (i.e., C33–C37 link) is at about 93° to the non-fluorinated region of the side chain and the second region (i.e., C37–C39 link) is at about 254.5° to the first link (both of these in view b). In a view similar to view c of FIG. 2, the bond of the O17 atom makes an angle of about 67° with the plane of the rings, the bond of C35 atom an angle of about 52°, and the bond of C37 atom of about −60°.

In all four compounds the oxygen of the hydroxyl group (O17 atom) makes almost a right angle to the side chain in the side view (−90° in propranolol and 1c and +90° in 1b and 1d, respectively, in a view similar to view b of FIG. 2).

There were mostly small changes in the geometry of the molecules with the introduction of the fluorine atoms, except near the side chain terminus. The geometries are illustrated in FIG. 3 with the molecules displayed along their longitudinal axes together with charges on individual atoms.

The most important dipole moments, bond angles and the torsion angles of propranolol and the fluorinated analogs may be obtained from the supplementary material in Tables S1–S3 herein.

Molecular Volumes

The sizes of the 4 molecules are not very different. In fact, there is a reduction in size from the parent to the 1st derivative (−CF$_3$). The dimensions of the molecule boxes together with the molecular volumes for the four molecules are as follows: propranolol 335.162 Å$^3$, trifluoroethyl propranolol 280.183 Å$^3$, pentafluoropropyl-propranolol 382.636 Å$^3$, and heptafluorobutyl propranolol 395.135 Å$^3$.

Energies

The various energies (total energies, minimum binding energies, heats of formation, ionization potentials) relevant for the molecules are given in Table 1. From the data presented above, it appears that the influence of the fluorine atoms is primarily at the terminal in the geometry of the molecules. With each addition of the CF$_2$ group the non-fluorinated portion of the side chain rotates about 180° about its axis. In their stable configurations the molecules are in the following order with respect to the values of the energies: for binding energies: 1b>1a>1c>1d; for total energies 1a>1b>1c>1d; and for heat of formation: 1a>1b>1c>1d. For the values of the energies see the above-mentioned tables.

The ionization potentials of the four compounds discussed in this paper are almost the same (they differ in the second decimal place). As far as is known to the authors there does not seem to be a precedence of this in other series of polyfluoroalkyl amines.

The heat of formation of the "CF$_2$" increment group may be estimated and turns out to be in the range of −97.3 kcal/mol to −109.7 kcal/mol, with a mean of −103.5 kcal/mol. Heat of formation attributable to CF$_3$ may be estimated to be approximately −160 kcal/mol. Given the heat of formation of propranolol (−58 kcal/mol), the estimated heats of formation for the three derivatives from these figures come out to be −218 kcal/mol, −321 kcal/mol and −424 kcal/mol which are not significantly different from the respective values obtained from the AM1 calculations (given in Table 1 below).

Dipole Moment

The molecules do exhibit a sudden increase in the dipole moment from 1.303 Debyes to 4.142 Debyes when the two terminal methyl groups are replaced one by a hydrogen and the other by a −CF$_3$ group in 1b. With further addition of fluorines there is a further increase in the dipole moment (to 4.162 and then to 4.497 Debyes), but not as dramatic. This simple measure indicates a significant redistribution of charge density. To quantify this change further, charge distributions and electrostatic potentials were studied and are discussed below.

Charge Distributions

The changes in the charges distribution in the four compounds involve the ether oxygen (O11) and all the terminal fluorines. In propranolol most of the charge is concentrated on the ether oxygen. In 1b, the charge is most distributed around the same oxygen and the terminal fluorines and to a lesser extent around the nitrogen. In 1c and 1d, charge distribution is again mostly around the ether oxygen (O11) and the terminal fluorines and to a lesser extent around the hydroxyl oxygen (O17) and the nitrogen. The charge density distribution in the different molecules is shown in FIG. 4.

Electrostatic Potential

The sites of most negative electrostatic potential move towards the terminal of the molecules from the parent to the derivatives as the number of fluorines increase. In propranolol the site is near the ether oxygen, in 1b it is more or less equally distributed between the ether oxygen and the fluorinated terminal, in 1c the region of influence of the electrostatic potential progressively increases as it does again in 1d. The volume of this influence covers the region occupied by the nitrogen and the terminal fluorines in the three derivatives, but the increase in the number of fluorines make this region bigger. Thus the most likely site of protonation or electrophilic attack move from the ether oxygen in the parent through equally likely at this oxygen and the terminal to more likely at the fluorinated portion of the side chain terminal particularly in 1d. The regions are similar to those suggested by the charge density. As the number of fluorines increase in the molecule the corresponding region of influence also increases and reactivity would be expected to be stronger (i.e., stronger bonds are more likely to form). It is possible the binding to the receptor involves both the ether oxygen and the fluorines.

The molecular volumes and ionization potentials for the four compounds are almost equal. Significant changes in the molecules occur in the dipole moments, charge densities and the electrostatic potentials. Probably, the contribution from the changes in the charge density are sufficient to explain the changes in the biological activity of the four compounds as the number of fluorines on the molecules increases. Their activity increases (the volumic region of negative influence) with the increase in the number of fluorines. Maps of electrostatic potential distributions are given in FIG. 5.

Anti-oxidant Activity

In FIGS. 6, 7, and 8, the following abbreviations have been used:

LPO—lipid peroxidation;
μM—micro-molar;
R.—oxygen free radical system;
DHF—dihydroxyfumarate;
Fe—iron;
ADP—adenosine diphosphate;
$EC_{50}$—effective concentration which inhibits 50% of membrane lipid peroxidation;
GSH—glutathione; and
PBS—phosphate-buffered saline.

To test the antioxidant activity of the analogs, isolated liver microsomal membranes (0.2 mg/ml) were resuspended in PBS. The membrane samples were pretreated for 20 minutes with or without the drugs, before adding the free radical components (R.), which consisted of DHF (0.83 mM) and Fe (25 μM $FeCl_3$) chelated by ADP (250 μM). After 15–20 minutes of oxidation, membrane peroxidation was measured by the TBA (thio-barbituric acid) method as described in Mak & Weglicki, Methods in Enzymology 234: 620–630, 1994. Drug effects are represented by the percentage of inhibition of the oxidation product formation. Liver microsomal membranes were isolated from homogenized liver tissue by differential centrifugation according to the procedure of Mak & Weglicki, Pharmacological Research 25: 25–30, 1992.

The oxygen free radical system generates oxygen radicals to oxidize rat liver membranes in the experiment whose results are shown in FIGS. 6 and 7, and to oxidize endothelial cell glutathione in the experiment whose results are shown in FIG. 8. In the experiments for FIGS. 6 and 7, oxygen radicals are generated by the addition of DHF, Fe, and ADP. In the experiment for FIG. 8, oxygen radicals are generated by the addition of DHF and Fe. The detailed procedure and methods were described in Mak & Weglicki Methods in Enzymology. 234: 620–630, 1994).

In FIGS. 6 and 7, and in Table 6, the items F-4, F-3, and F-2, are the preparations shown as 1b, 1c, and 1d, respectively, in FIG. 1, and are part of the present invention. H-4, H-3, and H-2 are the un-fluorinated forms of F-4, F-3, and F-2, respectively.

A review and comparison of FIGS. 6 and 7 shows that fluorination significantly increases the antioxidant activity of the propranolol analogs. As indicated in FIG. 6, the $EC_{50}$ (concentration of test compound which will inhibit membrane lipid peroxidation by 50%) is 196 μM for propranolol, but only 21 μM for F-2, 38 μM for F-3, and 62 μM for F-4, indicating that the fluorinated compounds are much more effective antioxidants.

The data in FIG. 8 demonstrate that while propranolol itself has a modest antioxidant effect, either F2-R (the form which is inactive as a beta-blocker) or a 50—50 mixture of F2-R and F2-S (active and inactive forms) are far more effective as antioxidants, providing more than 50% protection from the R.(DHF+Fe)-induced loss of endothelial cell glutathione at a concentration of 5 μM.

Table 6 shows the molecular structure of types of fluorinated propranolols, that are part of the present invention The parent compound, a variation of propranolol, is shown at the top of the Table. The -R structures of F-4, F-3, and F-2 (1b, 1c, and 1d, respectively), are shown, with other data Equivalent data for H-4, H-3, and H-2 (which are the unfluorinated forms of F-4, F-3, and F-2) are also shown. A the bottom of the table, the S (or left) enantiomer of F-2 is shown, as is the R- (right or D-) enantiomer of F-2. The inventors find that each right (or D) form of propranolol whether fluorinated or not, is not a beta blocker; and each S (or left) form of propranolol, whether fluorinated or not, is a beta blocker. Fluorination of each form increases it anti-oxidant effect, without changing its beta blocke potency, or lack of it. The anti-oxidant potency for eacl analog of propranolol is about the same for both the left an right form of that analog.

In FIGS. 6 and 7, racemic propranolol (50 percen D-propranolol and 50 percent C-propranolol) was used fo the control (un-fluorinated) propranolol.

In FIG. 8, the left-most column shows the GSH level o the endothelial cells ("Veh.") without radicals or propranolc treatment. The second column ("R.") shows a 50 percen loss of the GSH caused by treatment with the radical syster only. The third column ("+Prop.") shows treatment of th cells (with radicals R.) with racemic propranolol (50 percer D-propronolol and 50 percent L-propranolol) only. Th fourth column ("+F2") shows the effect of treating the cell (with radicals R.) with a racemic mixture of 50 percer Left-F-2, and 50 percent Right F-2. The fifth colum ("+F2R") shows the effect of treating the cells (with radical R.) with Right F-2.

In the third, fourth, and fifth columns, the drug (Propranolol, the 50/50 mixture, and F2R, respectively were each applied at a concentration of 5 micromolar.

The fluorinated forms of propranolol of the present inver tion can be used to treat any disease that is responsive t anti-oxidant treatment. The right (or D-) forms of th fluorinated propranolols would be especially indicated fc treatment where beta-blocker effects or toxicity are antic pated as a problem.

Active beta blockers bind to the beta adrenergic receptor with high affinity whereas inactive compositions (non-be blockers) will not.

Method of Synthesis

The synthesis of these compounds was achieved by tl reaction of the glycidic ether (epoxide) namely, 1'-(2: epoxypropoxy)naphthalene with the appropriate fluorinat( amine. Opening of the oxirane ring with these fluorinat( amines gives the fluorinated propranolol analogs described below.

SYNTHESIS OF (2RS) 1'-(2,3-EPOXYPROPOXY) NAPHTHALENE:

SYNTHESIS OF (2RS)-1'-(2,3-EPOXYPROPOXY)NAPHTHALENE:

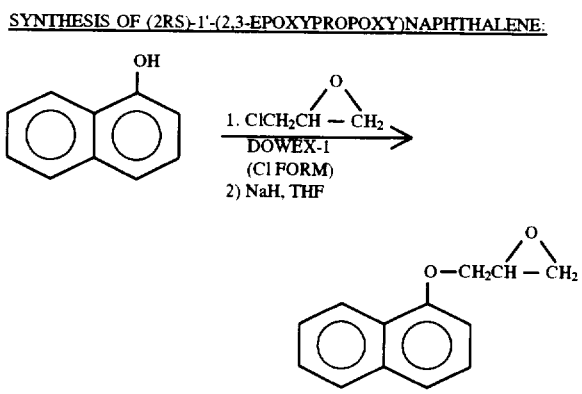

A method described by Oatis et al (see, J. E. Oatis, Jr., J. P. Baker, J. R. McCarthy, and D. R. Knapp, J. Med. Chem., 26,1687–1691 (1983)), was adopted for the synthesis of this intermediate. A mixture of 1-naphthol (0.5 mole) and 72 g of Dowex resin (chloride form) was refluxed for 2 hours in epichlorohydrin (400 ml, 5.19 mole). The reaction mixture was cooled to room temperature, and the resin was removed by filteration. Excess epichlorohydrin was removed under vacuum, toulene (100 ml) was added and then distilled in vacuum. The residue was added dropwise to sodium hydride (18 g of 50% mineral oil dispersion) suspended in cold dry tetrahydrofuran (100 ml). After the addition was completed, the reaction mixture was filtered and concentrated. The residue was dissolved in ether and the resulting precipitate was removed by filteration. The filterate washed twice with 50 ml of 10% sodium hydroxide solution, followed by 50 ml of water and twice with 50 ml of brine and dried over anhydrous potassium carbonate then filtered. The ethereal filterate was removed under vacuum where a yellow orange liquid (86 g) was left. The product was then purified by fractional distillation at 64 C at 0.015 mmHg to give 68 g of the product as a colorless liquid.

THE SYNTHESIS OF THE FLUORINATED PROPRANOLOL ANALOGS
(RS)-1-(2.2.2-TRIFLUOROETHYLAMINO)-3-(1-NAPHTHYLOXY)-2-PROPANOL

(RS)-1-(2,2,2-TRIFLUOROETHYLAMINO)-3-(1-NAPHTHYLOXY)-2-PROPANOL:

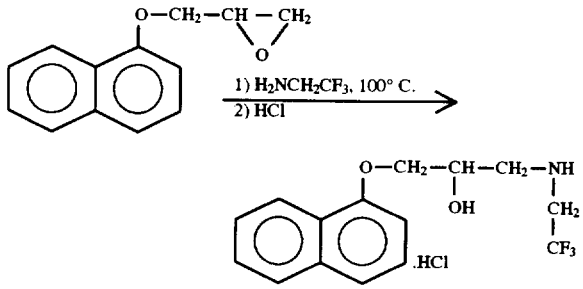

A mixture of (2RS)-1'-(2,3-epoxypropoxy)naphthalene (1.4 g, 6.49 mmole) and 2,2,2,-trifluroethylamine (25 g, 252.4 mmole) were heated in a sealed glass tube for about 115 hours at 100° C., Excess amine was distilled under vacuum and collected. The remaining solid was dissolved in ether and washed twice with 250 ml of water. The ethereal solution was treated with dry hydrogen chloride gas to convert the amine to its hydrochloride salt which is collected as a off white solid ; m.p. 178°–180° C.; (yield 68%).

RS-1-(2,2,3,3,3-PENTAFLUOROPROPYLAMINO) -3-(1-NAPHTHYLOXY)-2-PROPANOL

(RS)-1-(2,2,3,3,3-PENTAFLUOROPROPYLAMINO)-3- (1-NAPHTHYLOXY)-2-PROPANOL:

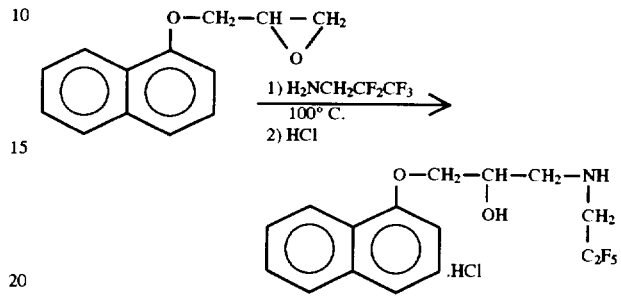

The same as described above but using (2RS)-1'-(2,3, epoxypropoxy) naphtalene (1.7 g, 8.5 mmole) and 2,2,3,3, 3-pentafluropropylamine (25 g, 170 mmole). The product is a white to off white solid, m.p. 227°–228° C., (yield 58%)

(RS)-1-(2,2,3,3,4,4,4-HEPTAFLUOROBUTYLAMINO)-3-(1-NAPHTHYLOXY)-2-PROPANOL

(RS)-1-(2,2,3,3,4,4,4-HEPTAFLUOROBUTYLAMINO)-3- (1-NAPHTHYLOXY)-2-PROPANOL:

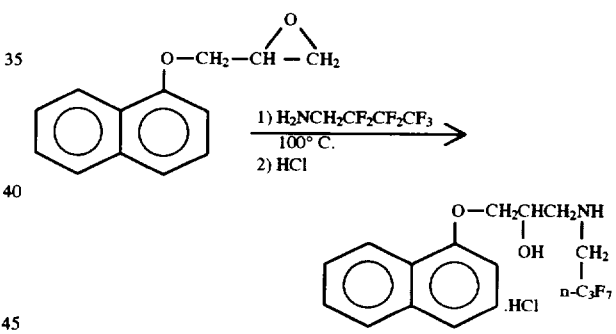

The same as described above but using (2RS)-1'-(2,3-epoxypropoxy)naphthalene ((1.3 g, 6.49 mmole) and 2,2,3, 3,4,4,4-hepafluorobutylamine (125,6 mmole). The hydrochloride salt obtained is a white to off white solid, m.p. 236°–237° C., (yield 67%).

Other Comments

Much of the discussion herein involves fluorinated forms of propranolol, included analogs of propranolol with and without beta blocking effect. However, the present invention may apply to any beta-blocker drug that has anti-oxidant effects there are amplified by fluorination, and analog forms without beta blocking effect that also have antioxidant effect that is amplified by fluorination.

The embodiments described herein are merely illustrative of the principles of this invention. Other arrangements and advantages may be devised by those skilled in the art without departing from the spirit and scope of the invention. Accordingly, the invention should be deemed not to be limited to the above detailed description but only by the spirit and scope of the claims which follow, and their equivalents.

TABLE 1

Optimized Energies of the Molecules

| S.Nr | Compound | Ionization Potential (eV) | Heat of Formation (kcal/mol) | Min. Binding Energy (kcal/mol) | Gradient (kcal/mol/Å) | Total Energy (kcal/mol) |
|---|---|---|---|---|---|---|
| 1 | Propranolol (1a) | −8.51 | −58.1 | −4118.6 | 0.0085 | −73462.6 |
| 2 | Trifluoroethyl-propranolol (1b) | −8.63 | −209.4 | −3895.2 | 0.0098 | −102505.3 |
| 3 | Pentafluoropropyl-propranolol (1c) | −8.63 | −302.0 | −4196.5 | 0.0096 | −127837.0 |
| 4 | Heptafluorobutyl-propranolol (1d) | −8.64 | −392.1 | −4495.2 | 0.0099 | −153166.1 |

15

TABLE 2

Coordinates of Propranolol (1a)

| Atom # | Atom | Charge (e⁻) | x coordinate (Å) | y coordinate (Å) | z coordinate (Å) |
|---|---|---|---|---|---|
| 1 | C | −0.095 | −0.372 | 3.301 | 0.0004 |
| 2 | C | −0.139 | −0.565 | 4.661 | −0.049 |
| 3 | C | −0.116 | 0.544 | 5.539 | −0.062 |
| 4 | C | −0.128 | 1.824 | 5.041 | −0.025 |
| 5 | C | −0.011 | 2.055 | 3.640 | 0.025 |
| 6 | C | −0.053 | 0.941 | 2.763 | 0.039 |
| 7 | C | 0.100 | 1.192 | 1.351 | 0.090 |
| 8 | C | −0.217 | 2.479 | 0.854 | 0.125 |
| 9 | C | −0.092 | 3.574 | 1.750 | 0.110 |
| 10 | C | −0.150 | 3.373 | 3.106 | 0.061 |
| 11 | O | −0.226 | 0.051 | 0.571 | 0.106 |
| 12 | C | −0.061 | 0.262 | −0.846 | 0.084 |
| 13 | C | 0.024 | −1.144 | −1.457 | 0.054 |
| 14 | C | −0.066 | −1.020 | −2.984 | −0.092 |
| 15 | N | −0.298 | −2.300 | −3.625 | −0.301 |
| 16 | C | −0.022 | −2.249 | −5.081 | −0.162 |
| 17 | O | −0.332 | −1.822 | −1.211 | 1.276 |
| 33 | C | −0.216 | −3.642 | −5.677 | 0.046 |
| 34 | C | −0.207 | −1.607 | −5.748 | −1.380 |

TABLE 3

Coordinates of Trifluoroethyl-propranolol (1b)

| Atom # | Atom | Charge (e⁻) | x coordinate (Å) | y coordinate (Å) | z coordinate (Å) |
|---|---|---|---|---|---|
| 1 | C | −0.096 | −0.368 | 3.314 | −0.010 |
| 2 | C | −0.137 | −0.562 | 4.674 | 0.036 |
| 3 | C | −0.115 | 0.546 | 5.553 | −0.037 |
| 4 | C | −0.127 | 1.827 | 5.056 | −0.014 |
| 5 | C | −0.012 | 2.059 | 3.654 | 0.011 |
| 6 | C | −0.052 | 0.946 | 2.776 | 0.015 |
| 7 | C | 0.097 | 1.199 | 1.364 | 0.042 |
| 8 | C | −0.215 | 2.486 | 0.866 | 0.056 |
| 9 | C | −0.093 | 3.580 | 1.764 | 0.051 |
| 10 | C | −0.148 | 3.378 | 3.120 | 0.031 |
| 11 | O | −0.226 | 0.057 | 0.584 | 0.056 |
| 12 | C | −0.061 | 0.266 | −0.833 | 0.053 |
| 13 | C | 0.025 | −1.142 | −1.438 | 0.107 |
| 14 | C | −0.062 | −1.032 | −2.967 | −0.023 |

TABLE 3-continued

Coordinates of Trifluoroethyl-propranolol (1b)

| Atom # | Atom | Charge (e⁻) | x coordinate (Å) | y coordinate (Å) | z coordinate (Å) |
|---|---|---|---|---|---|
| 15 | N | −0.299 | −2.331 | −3.606 | −0.095 |
| 16 | C | −0.101 | −2.261 | −5.037 | 0.062 |
| 17 | O | −0.333 | −1.751 | −1.1716 | 1.360 |
| 33 | C | 0.410 | −3.676 | −5.698 | −0.082 |
| 34 | H | 0.125 | −1.614 | −5.465 | −0.753 |
| 35 | F | −0.172 | −3.629 | −7.057 | 0.114 |
| 36 | F | −0.168 | −4.599 | −5.245 | 0.826 |
| 37 | F | −0.155 | −4.266 | −5.541 | −1.305 |

TABLE 4

Coordinates of Pentafluoropropyl-Propranolol (1c)

| Atom # | Atom | Charge (e⁻) | x coordinate (Å) | y coordinate (Å) | z coordinate (Å) |
|---|---|---|---|---|---|
| 1 | C | −0.096 | −11.416 | −14.006 | 17.181 |
| 2 | C | −0.137 | −11.611 | −12.645 | 17.180 |
| 3 | C | −0.115 | −10.503 | −11.766 | 17.165 |
| 4 | C | −0.127 | −9.222 | −12.263 | 17.148 |
| 5 | C | −0.012 | −8.989 | −13.665 | 17.145 |
| 6 | C | −0.052 | −10.102 | −14.543 | 17.164 |
| 7 | C | 0.097 | −9.849 | −15.956 | 17.164 |
| 8 | C | −0.215 | −8.562 | −16.453 | 17.135 |
| 9 | C | −0.093 | −7.469 | −15.556 | 17.116 |
| 10 | C | −0.148 | −7.670 | −14.199 | 17.123 |
| 11 | O | −0.226 | −10.991 | −16.734 | 17.197 |
| 12 | C | −0.060 | −10.786 | −18.151 | 17.177 |
| 13 | C | 0.025 | −12.194 | −18.748 | 17.288 |
| 14 | C | −0.060 | −12.106 | −20.276 | 17.130 |
| 15 | N | −0.306 | −13.413 | −20.9012 | 17.127 |
| 16 | C | −0.104 | −13.355 | −22.336 | 17.247 |
| 17 | O | −0.334 | −12.739 | −18.495 | 18.574 |
| 33 | C | 0.239 | −14.782 | −22.965 | 17.148 |
| 34 | H | 0.127 | −12.747 | −22.751 | 16.395 |
| 35 | F | −0.139 | −15.577 | −22.641 | 18.220 |
| 36 | F | −0.139 | −14.721 | −24.337 | 17.207 |
| 37 | C | 0.389 | −15.505 | −22.512 | 15.781 |
| 38 | F | −0.138 | −16.090 | −21.282 | 15.870 |
| 39 | F | −0.152 | −16.505 | −23.369 | 15.410 |
| 40 | F | −0.147 | −14.656 | −22.463 | 14.713 |

TABLE 5

Coordinates of Heptafluorobutyl-Propranolol (1d)

| Atom # | Atom | Charge (e) | x coordinate (Å) | y coordinate (Å) | z coordinate (Å) |
|---|---|---|---|---|---|
| 1 | C | −0.096 | −6.728 | −8.879 | 18.236 |
| 2 | C | −0.137 | −6.906 | −7.516 | 18.233 |
| 3 | C | −0.115 | −5.787 | −6.650 | 18.222 |
| 4 | C | −0.127 | −4.512 | −7.163 | 18.212 |
| 5 | C | −0.012 | −4.297 | −8.568 | 18.213 |
| 6 | C | −0.052 | −5.420 | −9.432 | 18.226 |
| 7 | C | 0.097 | −5.184 | −10.848 | 18.227 |
| 8 | C | −0.215 | −3.903 | −11.360 | 18.207 |
| 9 | C | −0.093 | −2.799 | −10.476 | 18.195 |
| 10 | C | −0.147 | −2.984 | −9.117 | 18.199 |
| 11 | O | −0.226 | −6.335 | −11.614 | 18.251 |
| 12 | C | −0.061 | −6.144 | −13.032 | 18.224 |
| 13 | C | 0.024 | −7.557 | −13.621 | 18.312 |
| 14 | C | −0.062 | −7.470 | −15.150 | 18.159 |
| 15 | N | −0.302 | −8.775 | −15.780 | 18.158 |
| 16 | C | −0.102 | −8.706 | −17.208 | 18.344 |
| 17 | O | −0.334 | −8.123 | −13.363 | 19.587 |
| 33 | C | 0.238 | −10.131 | −17.854 | 18.375 |
| 34 | H | 0.127 | −8.150 | −17.661 | 17.476 |
| 35 | F | −0.137 | −10.867 | −17.441 | 19.460 |
| 36 | F | −0.140 | −10.039 | −19.214 | 18.559 |
| 37 | C | 0.214 | −10.936 | −17.529 | 17.023 |

TABLE 5-continued

Coordinates of Heptafluorobutyl-Propranolol (1d)

| Atom # | Atom | Charge (e) | x coordinate (Å) | y coordinate (Å) | z coordinate (Å) |
|---|---|---|---|---|---|
| 38 | F | −0.111 | −11.471 | −16.271 | 17.052 |
| 39 | C | 0.379 | −12.118 | −18.614 | 16.809 |
| 40 | F | −0.119 | −10.117 | −17.527 | 15.927 |
| 41 | F | −0.140 | −13.025 | −18.210 | 15.871 |
| 42 | F | −0.137 | −12.831 | −18.855 | 17.946 |
| 43 | F | −0.139 | −11.648 | −19.822 | 16.382 |

TABLE 6

FLUORINATED PROPRANOLOL ANALOGS:

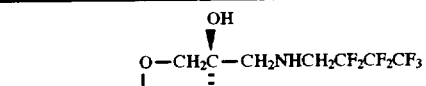

PARENT COMPOUND

| Code NO. | −R | MW (as a base) | Mol. Formula |
|---|---|---|---|
| 1B F-4 | −CH$_2$CF$_3$ | 299.26 | C$_{15}$H$_{16}$F$_3$NO$_2$ |
| 1C F-3 | −CH$_2$CF$_2$CF$_3$ | 349.25 | C$_{16}$H$_{16}$F$_5$NO$_2$ |
| 1D F2 | −CH$_2$CF$_2$CF$_2$CF$_3$ | 399.3 | C$_{17}$H$_{16}$F$_7$NO$_2$ |
| H-4 | −CH$_2$CH$_3$ | 245.3 | C$_{15}$H$_{19}$NO$_2$ |
| H-3 | −CH$_2$CH$_2$CH$_3$ | 259.35 | C$_{16}$H$_{21}$NO$_2$ |
| H-2 | −CH$_2$CH$_2$CH$_2$CH$_3$ | 273.35 | C$_{17}$H$_{23}$NO$_2$ |

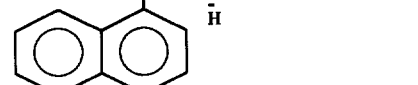

(−)-S-Enantiomer Compound F$_2$
B BLOCKER
(LEFT)
(L)

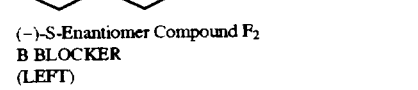

(+)-R-Enantiomer Compound F$_2$
NOT B BLOCKER
(RIGHT)
(D)

TABLE S1

Important Bond Angles (°) for the Fluorinated Analogs

| S.Nr | Relevant Atoms | Trifluoroethyl-Propranolol (1b) | Pentafluoropropyl-Propranolol (1c) | Heptafluorobutyl-Propranolol (1d) |
|---|---|---|---|---|
| 1 | C14-N15-C16 | 112.9 | 113.1 | 112.8 |
| 2 | N15-C16-C33 | 111.4 | 111.0 | 111.6 |
| 3 | N15-C16-H34 | 109.1 | 109.0 | 108.8 |
| 4 | C33-C16-H34 | 107.0 | 107.3 | 107.4 |
| 5 | C16-C33-F35 | 111.9 | 112.6 | 112.3 |
| 6 | C16-C33-F36 | 114.0 | 111.0 | 110.4 |
| 7 | C16-C33-F37 | 115.0 | -NA- | -NA- |
| 8 | C16-C33-C37 | -NA- | 110.5 | 110.9 |
| 9 | F35-C33-F36 | 104.8 | 103.2 | 103.1 |
| 10 | F35-C33-F37 | 104.9 | -NA- | -NA- |
| 11 | F36-C33-F37 | 105.3 | -NA- | -NA- |
| 12 | F35-C33-C37 | -NA- | 109.6 | 109.6 |
| 13 | F36-C33-C37 | -NA- | 109.7 | 110.3 |
| 14 | C33-C37-F38 | -NA- | 113.0 | 111.4 |
| 15 | C33-C37-F39 | -NA- | 112.4 | 110.0 |
| 16 | C33-C37-F40 | -NA- | 113.2 | 112.0 |
| 17 | F38-C33-F39 | -NA- | 105.6 | -NA- |
| 18 | F38-C33-C39 | -NA- | -NA- | 109.5 |
| 19 | F38-C33-F40 | -NA- | 106.5 | 104.5 |
| 20 | F39-C33-F40 | -NA- | 105.4 | 109.4 |
| 21 | C37-C39-F41 | -NA- | -NA- | 112.2 |
| 22 | C37-C39-F42 | -NA- | -NA- | 113.0 |
| 23 | C37-C39-F43 | -NA- | -NA- | 112.5 |
| 24 | F41-C39-F42 | -NA- | -NA- | 106.1 |
| 25 | F41-C39-F43 | -NA- | -NA- | 106.1 |
| 26 | F42-C39-F43 | -NA- | -NA- | 106.5 |

*NA means not applicable.

TABLE S2

Important Torsion Angles (°) for the Fluorinated Analogs

| S.Nr | Relevant Atoms | Trifluoroethyl-Propranolol (1b) | Pentafluoropropyl-Propranolol (1c) | Heptafluorobutyl-Propranolol (1d) |
|---|---|---|---|---|
| 1 | C14-N15-C16-C33 | −177.6 | −176.5 | 178.4 |
| 2 | C14-N15-C16-H34 | −59.7 | −58.5 | −63.3 |
| 3 | C15-C16-C33-F35 | -NA- | −67.3 | −65.1 |
| 4 | C15-C16-C33-F36 | -NA- | 177.5 | −179.7 |
| 5 | C15-C16-C33-C37 | -NA- | 55.6 | 57.8 |
| 6 | C16-C33-C37-F38 | -NA- | −82.5 | −79.8 |
| 7 | C16-C33-C37-F39 | -NA- | −158.1 | -NA- |
| 8 | C16-C33-C37-C39 | -NA- | -NA- | 158.6 |
| 9 | C16-C33-C37-F40 | -NA- | 38.8 | 36.7 |
| 10 | C35-C33-C37-F38 | -NA- | 42.1 | 44.6 |
| 11 | C35-C33-C37-F39 | -NA- | −77.3 | -NA- |
| 12 | C35-C33-C37-C39 | -NA- | -NA- | −76.9 |
| 13 | C35-C33-C37-F40 | -NA- | 163.4 | 161.2 |
| 14 | C36-C33-C37-F38 | -NA- | 154.8 | 157.5 |
| 15 | C36-C33-C37-F39 | -NA- | 35.4 | -NA- |
| 16 | C36-C33-C37-C39 | -NA- | -NA- | 36.0 |
| 17 | C36-C33-C37-F40 | -NA- | −84.0 | −85.9 |
| 18 | C33-C37-C39-F41 | -NA- | -NA- | 165.4 |
| 19 | C33-C37-C39-C42 | -NA- | -NA- | 45.5 |
| 20 | C33-C37-C39-C43 | -NA- | -NA- | −75.1 |
| 21 | F38-C37-C39-F41 | -NA- | -NA- | 42.7 |
| 22 | F38-C37-C39-F42 | -NA- | -NA- | −77.2 |
| 23 | F38-C37-C39-F43 | -NA- | -NA- | 162.2 |
| 24 | F40-C37-C39-F41 | -NA- | -NA- | −71.3 |
| 25 | F40-C37-C39-F42 | -NA- | -NA- | 168.9 |
| 26 | F40-C37-C39-F43 | -NA- | -NA- | 48.2 |

*NA means not applicable.

TABLE S3

Dipole Moments of the Molecules

| Sr.Nr | Compound | x | y | z | Total Dipole Moment (Debyes) |
|---|---|---|---|---|---|
| 1 | Propranolol (1a) | 1.262 | −0.326 | 0.034 | 1.303 |
| 2 | Trifluoroethyl-propranolol (1b) | 3.851 | 1.508 | 0.236 | 4.142 |
| 3 | Pentafluoropropyl-propranolol (1c) | 3.927 | 1.249 | 0.578 | 4.162 |
| 4 | Heptafluorobutyl-propranolol (1d) | 4.152 | 1.704 | 0.280 | 4.497 |

We claim:

1. A compound of formula

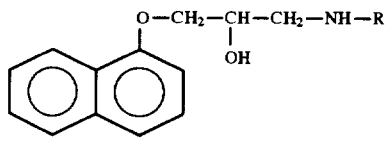

wherein R represents a straight or branched chain alkyl group of 1–6 carbon atoms which is substituted with at least one fluorine atom.

2. The compound of claim 1 which has activity as a β-adrenergic blocker.

3. The compound of claim 1 which is inactive as a β-adrenergic blocker.

4. The compound of claim 1 which is an L-isomer.

5. The compound of claim 1 which is a D-isomer.

6. A composition comprising the compound of claim 2 and the compound of claim 3.

7. The composition of claim 6 wherein the ratio of the compound of claim 2 to the compound of claim 3 is between about 0.01 and 0.2.

8. The composition of claim 7 wherein the ratio is between about 0.05 and 0.1.

9. The compound of claim 1 wherein R is selected from the group consisting of $-CH_2CF_3$, $-CH_2CF_2CF_3$ and $-CH_2CF_2CF_2CF_3$.

10. The compound of claim 9 which is active as a β-adrenergic blocker.

11. The compound of claim 9 which is inactive as a β-adrenergic blocker.

12. A composition comprising the compound of claim 10 and the compound of claim 11.

13. The composition of claim 12 wherein the ratio of the compound of claim 10 to the compound of claim 11 is between about 0.01 and 0.2.

14. The composition of claim 13 wherein the ratio is between about 0.05 and 0.1.

15. The compound of claim 9 which is a D-isomer.

16. The compound of claim 9 which is an L-isomer.

17. A method of treating a disease or disorder of the cardiovascular system comprising administering to an individual the compound of claim 1.

18. A method of treating a disease or disorder of the cardiovascular system comprising administering to an individual the composition of claim 6.

19. The method of claim 18 wherein said disease or disorder is selected from the group consisting of heart failure, myocardial infarction, atherosclerosis, stroke, hypertension and ischemia/reperfusion injury.

20. A method of treating a disease or disorder of the cardiovascular system comprising administering to an individual the compound of claim 9.

21. A method of treating a disease or disorder of the cardiovascular system comprising administering to an individual the composition of claim 12.

* * * * *